(12) United States Patent
Retter et al.

(10) Patent No.: US 9,588,038 B2
(45) Date of Patent: Mar. 7, 2017

(54) ANALYTICAL SYSTEM WITH CAPILLARY TRANSPORT

(71) Applicant: Beckman Coulter, Inc., Brea, CA (US)

(72) Inventors: Robert Retter, Buena Park, CA (US); Yagang Liu, Yorba Linda, CA (US); Patty Pang, Brea, CA (US); Brian Peterson, Ontario, CA (US)

(73) Assignee: Beckman Coulter, Inc., Brea, CA (US)

( * ) Notice: Subject to any disclaimer, the term of this patent is extended or adjusted under 35 U.S.C. 154(b) by 54 days.

(21) Appl. No.: 14/641,217

(22) Filed: Mar. 6, 2015

(65) Prior Publication Data
US 2015/0177123 A1 Jun. 25, 2015

Related U.S. Application Data

(63) Continuation of application No. 14/026,358, filed on Sep. 13, 2013, now Pat. No. 9,007,574.
(Continued)

(51) Int. Cl.
*G01N 21/01* (2006.01)
*G01N 21/03* (2006.01)
(Continued)

(52) U.S. Cl.
CPC .............. *G01N 21/03* (2013.01); *G01N 21/01* (2013.01); *G01N 21/59* (2013.01);
(Continued)

(58) Field of Classification Search
CPC ... G01N 2035/1039; G01N 2035/1062; G01N 35/04; G01N 35/10; G01N 35/1065;
(Continued)

(56) References Cited

U.S. PATENT DOCUMENTS

| 4,401,189 A | 8/1983 | Majewski |
| 4,530,056 A | 7/1985 | MacKinnon et al. |

(Continued)

FOREIGN PATENT DOCUMENTS

| DE | 1 175 604 | 8/1964 |
| DE | 35 10 797 C2 | 1/1988 |

(Continued)

OTHER PUBLICATIONS

Caprari, G. et al.; "The autonomous Micro Robot "Alice": a platform for scientific and commercial applications"; Proceedings of the 1998 International Symposium on Micromechatronics and Human Science, Nagoya, Japan; Nov. 25-28, 1998; pp. 1-5.
(Continued)

*Primary Examiner* — Michael P Stafira
(74) *Attorney, Agent, or Firm* — Kilpatrick Townsend & Stockton LLP

(57) ABSTRACT

An analytical system is disclosed. The analytical system includes a storage container configured to store a plurality of capillaries. It also includes a gripper configured to receive at least one of the plurality of capillaries, and move the at least one capillary so that an end of the capillary contacts a sample in a sample container and draws the sample in the capillary. The system also includes a reader configured to detect a signal from the sample in the capillary.

20 Claims, 18 Drawing Sheets

Related U.S. Application Data

(60) Provisional application No. 61/701,360, filed on Sep. 14, 2012.

(51) Int. Cl.

| | | |
|---|---|---|
| *G01N 35/00* | (2006.01) | |
| *G01N 35/04* | (2006.01) | |
| *G01N 35/10* | (2006.01) | |
| *G01N 21/59* | (2006.01) | |

(52) U.S. Cl.
CPC ......... *G01N 35/0099* (2013.01); *G01N 35/04* (2013.01); *G01N 35/10* (2013.01); *G01N 2021/0346* (2013.01); *G01N 2035/0465* (2013.01); *G01N 2035/1039* (2013.01); *G01N 2035/1062* (2013.01); *G01N 2201/02* (2013.01); *G01N 2201/062* (2013.01)

(58) Field of Classification Search
CPC ....... G01N 35/0099; G01N 2021/0346; G01N 2035/00564; G01N 2035/00574; G01N 2035/1034; G01N 2035/1051; G01N 2035/1055
See application file for complete search history.

(56) References Cited

U.S. PATENT DOCUMENTS

| | | | |
|---|---|---|---|
| 4,593,238 | A | 6/1986 | Yamamoto |
| 4,593,239 | A | 6/1986 | Yamamoto |
| 4,780,817 | A | 10/1988 | Lofgren |
| 4,919,054 | A | 4/1990 | Matsuo |
| 4,947,094 | A | 8/1990 | Dyer et al. |
| 5,075,853 | A | 12/1991 | Luke, Jr. |
| 5,118,191 | A | 6/1992 | Hopkins |
| 5,168,766 | A | 12/1992 | Stoffel |
| 5,179,329 | A | 1/1993 | Nishikawa et al. |
| 5,205,393 | A | 4/1993 | Malow et al. |
| 5,244,055 | A | 9/1993 | Shimizu |
| 5,283,739 | A | 2/1994 | Summerville et al. |
| 5,351,801 | A | 10/1994 | Markin et al. |
| 5,366,896 | A | 11/1994 | Margrey et al. |
| 5,375,898 | A | 12/1994 | Ohmori et al. |
| 5,388,682 | A | 2/1995 | Dudley |
| 5,504,345 | A | 4/1996 | Bartunek et al. |
| 5,582,796 | A | 12/1996 | Carey et al. |
| 5,612,525 | A | 3/1997 | Apter et al. |
| 5,623,415 | A | 4/1997 | O'Bryan et al. |
| 5,652,489 | A | 7/1997 | Kawakami |
| 5,734,468 | A | 3/1998 | McNeal |
| 5,814,008 | A | 9/1998 | Chen et al. |
| 5,814,276 | A | 9/1998 | Riggs |
| 5,814,961 | A | 9/1998 | Imahashi |
| 5,881,781 | A | 3/1999 | Bishop |
| 5,884,746 | A | 3/1999 | Leisner et al. |
| 5,897,090 | A | 4/1999 | Smith et al. |
| 5,966,309 | A | 10/1999 | O'Bryan et al. |
| 6,011,508 | A | 1/2000 | Perreault et al. |
| 6,049,745 | A | 4/2000 | Douglas et al. |
| 6,056,106 | A | 5/2000 | van Dyke, Jr. et al. |
| 6,060,022 | A | 5/2000 | Pang et al. |
| 6,102,249 | A | 8/2000 | Sjoboen |
| 6,212,448 | B1 | 4/2001 | Xydis |
| 6,368,872 | B1 | 4/2002 | Juranas |
| 6,370,452 | B1 | 4/2002 | Pfister |
| 6,374,989 | B1 | 4/2002 | van Dyke, Jr. et al. |
| 6,377,888 | B1 | 4/2002 | Olch |
| 6,429,016 | B1 | 8/2002 | McNeil |
| 6,458,324 | B1 | 10/2002 | Schinzel |
| 6,520,313 | B1 | 2/2003 | Kaarakainen et al. |
| 6,586,255 | B1 | 7/2003 | Hubert et al. |
| 6,599,476 | B1 | 7/2003 | Watson et al. |
| 6,629,028 | B2 | 9/2003 | Paromtchik et al. |
| 6,770,883 | B2 | 8/2004 | McNeal et al. |
| 6,941,200 | B2 | 9/2005 | Sonoyama et al. |
| 6,993,176 | B2 | 1/2006 | Yamagishi et al. |
| 6,999,847 | B2 | 2/2006 | Barry et al. |
| 7,028,831 | B2 | 4/2006 | Veiner |
| 7,078,698 | B2 | 7/2006 | Itoh |
| 7,174,836 | B2 | 2/2007 | Marino et al. |
| 7,269,480 | B2 | 9/2007 | Hashimoto et al. |
| 7,362,258 | B2 | 4/2008 | Kawabe et al. |
| 7,463,948 | B2 | 12/2008 | Orita |
| 7,473,897 | B2 | 1/2009 | Braendle et al. |
| 7,499,581 | B2 | 3/2009 | Tribble et al. |
| 7,688,448 | B2 | 3/2010 | Bamberg et al. |
| 7,771,659 | B2 | 8/2010 | Ziegler |
| 8,021,611 | B2 * | 9/2011 | Roach .................... G01N 35/04 422/562 |
| 8,074,578 | B2 | 12/2011 | Thornton |
| 2002/0146347 | A1 | 10/2002 | McNeil |
| 2004/0158355 | A1 | 8/2004 | Holmqvist et al. |
| 2005/0163354 | A1 | 7/2005 | Ziegler |
| 2006/0006066 | A1 | 1/2006 | Yamazaki et al. |
| 2006/0014295 | A1 | 1/2006 | Ziegler |
| 2006/0020370 | A1 | 1/2006 | Abramson |
| 2006/0292558 | A1 | 12/2006 | O'Neill |
| 2007/0044676 | A1 | 3/2007 | Clark et al. |
| 2007/0059209 | A1 | 3/2007 | Pang et al. |
| 2007/0100498 | A1 | 5/2007 | Matsumoto et al. |
| 2007/0179690 | A1 | 8/2007 | Stewart |
| 2007/0193859 | A1 | 8/2007 | Kyutoku et al. |
| 2007/0208440 | A1 | 9/2007 | Bliss et al. |
| 2007/0225901 | A1 | 9/2007 | Yamaguchi |
| 2007/0225906 | A1 | 9/2007 | Ikeda |
| 2008/0167817 | A1 | 7/2008 | Hessler et al. |
| 2008/0297769 | A1 | 12/2008 | Bamberg et al. |
| 2009/0030551 | A1 | 1/2009 | Hein et al. |
| 2009/0263290 | A1 | 10/2009 | Yang et al. |
| 2009/0324032 | A1 | 12/2009 | Chen |
| 2010/0092683 | A1 | 4/2010 | Ermantraut et al. |
| 2010/0291619 | A1 * | 11/2010 | Robinson .................. C12Q 1/04 435/34 |
| 2010/0303331 | A1 | 12/2010 | Itoh |
| 2011/0011740 | A1 | 1/2011 | Roach et al. |
| 2011/0226584 | A1 | 9/2011 | Ek |
| 2012/0213667 | A1 | 8/2012 | Roach et al. |
| 2013/0167937 | A1 | 7/2013 | Roach et al. |
| 2013/0239665 | A1 | 9/2013 | Loppacher et al. |
| 2014/0078501 | A1 | 3/2014 | Retter et al. |

FOREIGN PATENT DOCUMENTS

| | | |
|---|---|---|
| DE | 696 33 532 T2 | 2/2006 |
| EP | 0 260 136 A2 | 3/1988 |
| EP | 0 260 136 A3 | 3/1988 |
| EP | 0 656 864 B1 | 3/1996 |
| EP | 0 727 665 A2 | 8/1996 |
| EP | 0 680 883 B1 | 12/1998 |
| EP | 1 034 418 A1 | 9/2000 |
| EP | 0 752 971 B1 | 6/2001 |
| EP | 1 288 758 B1 | 3/2003 |
| EP | 1 326 077 B1 | 9/2004 |
| EP | 1 557 961 A1 | 7/2005 |
| EP | 1 712 971 A2 | 10/2006 |
| EP | 1 712 971 A3 | 10/2006 |
| EP | 1 398 729 B1 | 10/2007 |
| EP | 1 721 671 B1 | 10/2009 |
| EP | 1 731 222 B1 | 3/2010 |
| EP | 2 148 205 B1 | 1/2013 |
| GB | 2 101 514 A | 1/1983 |
| GB | 2 158 425 A | 11/1985 |
| GB | 2 203 243 A | 10/1988 |
| JP | 06-011512 A | 1/1994 |
| JP | 07-049346 A | 2/1995 |
| JP | 07-213586 A | 8/1995 |
| JP | 07-301637 A | 11/1995 |
| JP | 08-285857 A | 11/1996 |
| JP | 08-286749 A | 11/1996 |
| JP | 09-021805 A | 1/1997 |
| JP | 09-080056 A | 3/1997 |
| JP | 09-089902 A | 4/1997 |
| JP | 09-89907 A | 4/1997 |

(56) References Cited

FOREIGN PATENT DOCUMENTS

| JP | 2007-249632 | A | 9/2007 |
|---|---|---|---|
| WO | 99/28724 | A1 | 6/1999 |
| WO | 00/15481 | A1 | 3/2000 |
| WO | 00/38046 | A1 | 6/2000 |
| WO | 00/67547 | A2 | 11/2000 |
| WO | 03/046412 | A1 | 6/2003 |
| WO | 2004/013640 | A1 | 2/2004 |
| WO | 2006/021052 | A1 | 3/2006 |
| WO | 2006/068470 | A1 | 6/2006 |
| WO | 2008/043393 | A1 | 4/2008 |
| WO | 2008/067847 | A1 | 6/2008 |
| WO | 2009/068555 | A1 | 6/2009 |
| WO | 2009/097263 | A1 | 8/2009 |
| WO | 2010/017528 | A2 | 2/2010 |
| WO | 2010/080340 | A1 | 7/2010 |
| WO | 2011/028166 | A1 | 3/2011 |
| WO | 2010/081606 | A1 | 7/2014 |

OTHER PUBLICATIONS

FLEXLINK®; "TX45E puck handling (mx. 250g),"; located at http://www.flexlink.com/en/offering/conveyor-systems/pallet-and-puck-handling/x45e.jsp; last visited on Jul. 20, 2013; 2 pages.

Kost, G. J., Handbook of Clinical Automation, Robotics, and Optimization; Chapters 1, 10, and 12-14; 1996 by John Wiley & Sons, Inc.; 189 pages total.

Magnemotion; "MagneMover™ LITE,"; located at http://www.magnemotion.com/industrial-automation/magmoverlite.cfm; last visited on Jul. 20, 2013; 3 pages.

Mondada, Francesco et al.; "The e-Puck, a Robot Designed for Education in Engineering", Proceedings of the 9th Conference on Autonomous Robot Systems and Competitions, Castelo Branco, Portugal; May 7, 2009; vol. 1; Issue 1; pp. 59-65.

International Search Report and Written Opinion mailed on Jan. 20, 2014 for PCT Patent Application No. PCT/US2013/059667, 10 pages.

\* cited by examiner

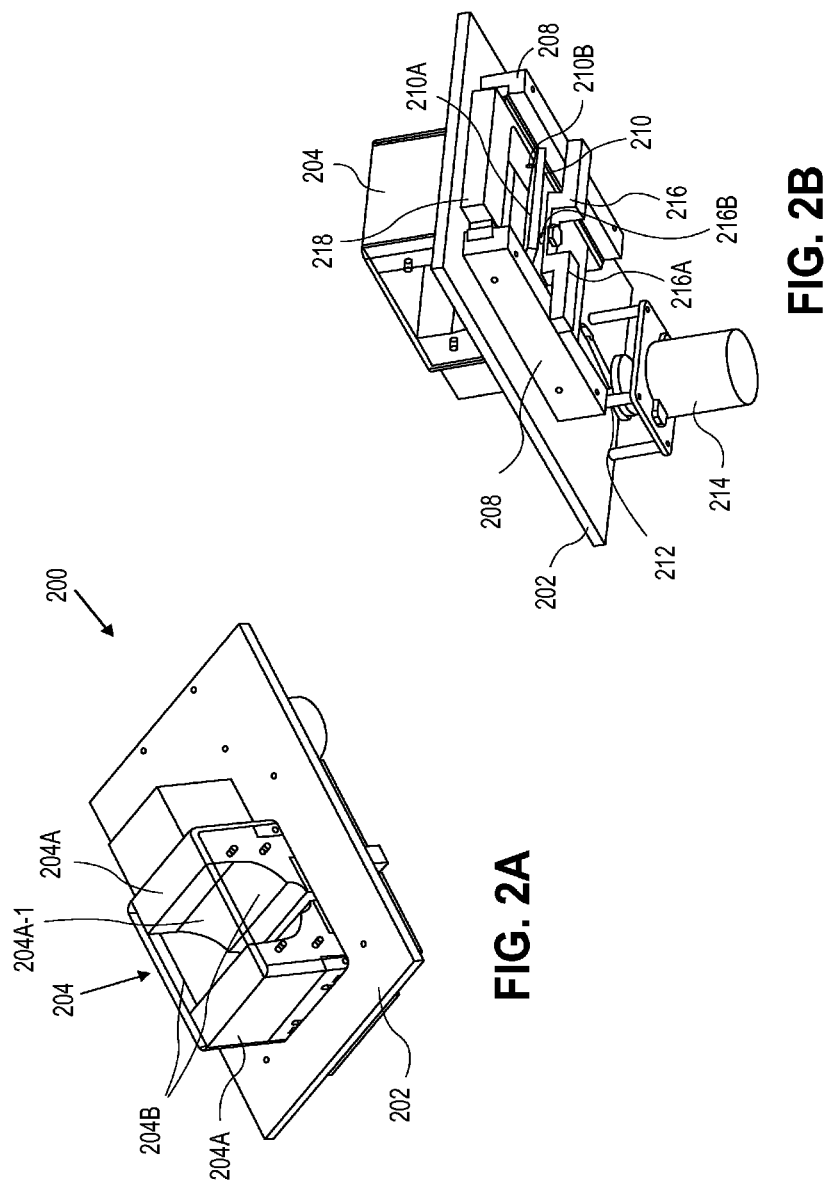

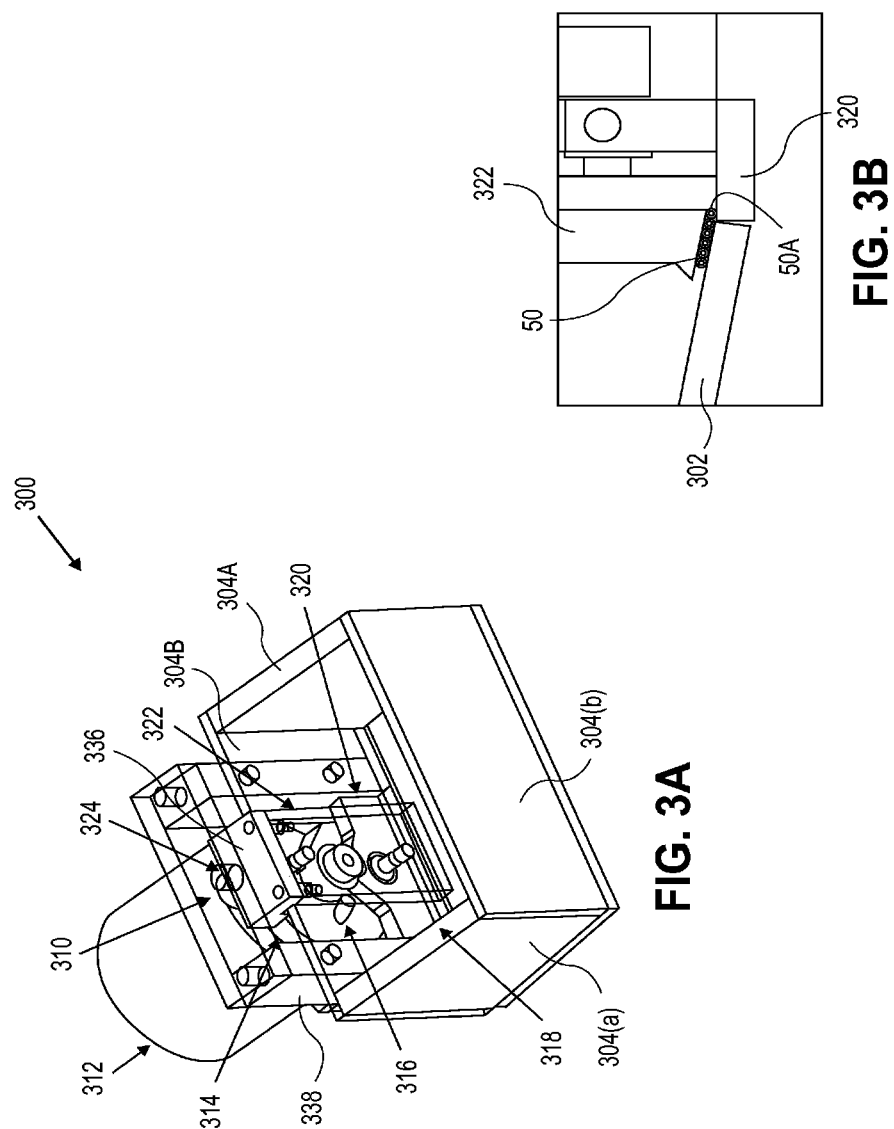

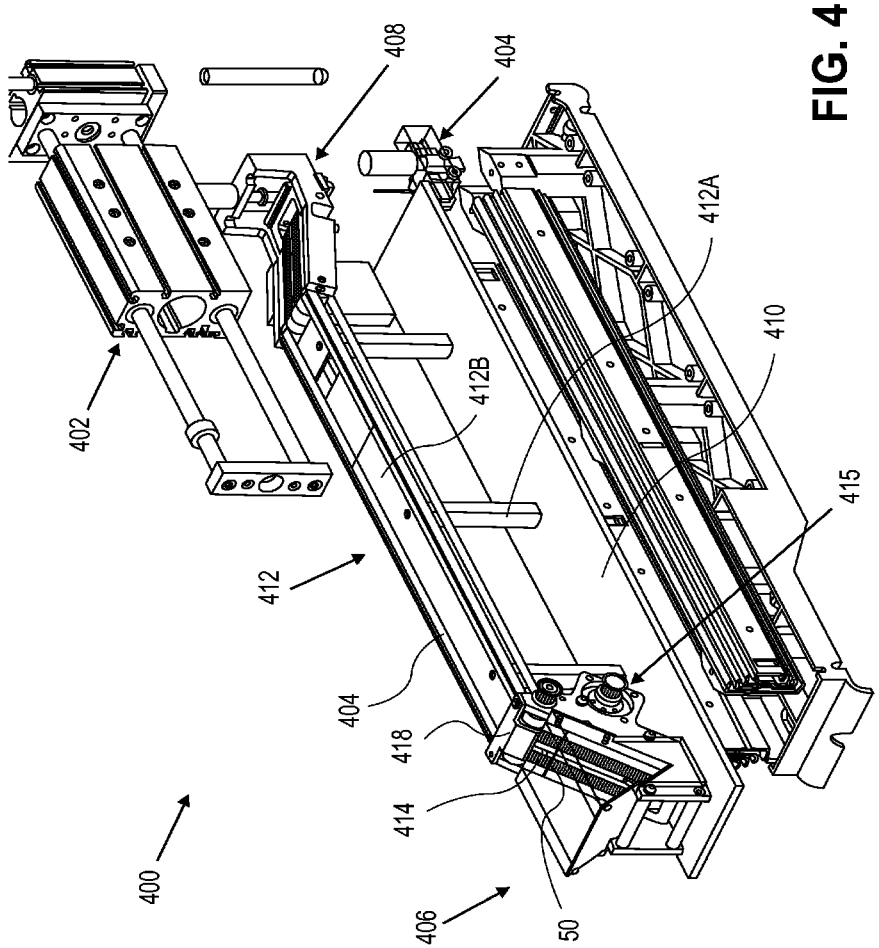

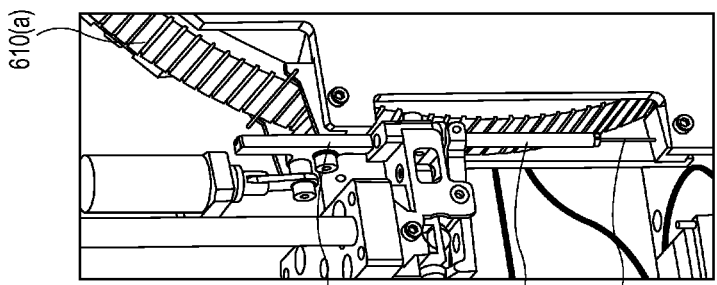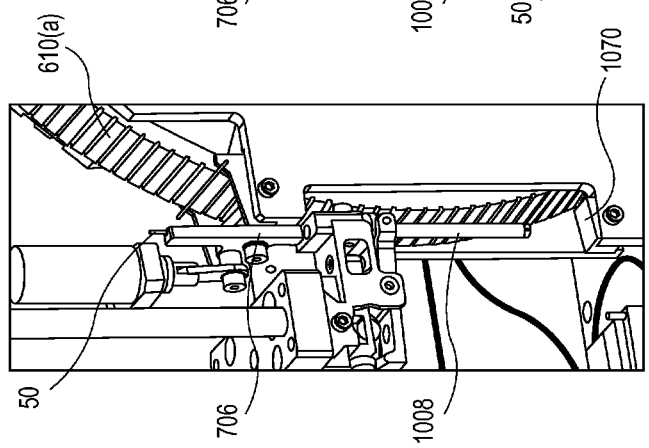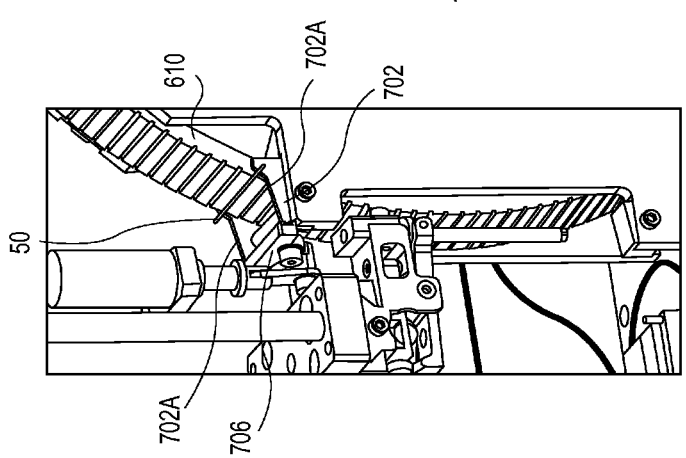

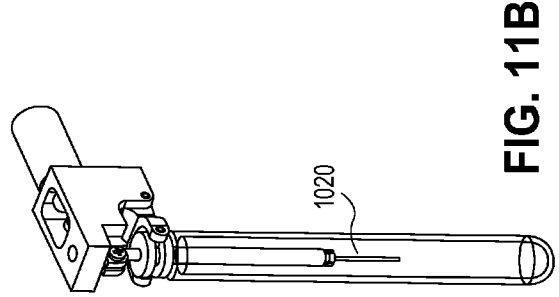
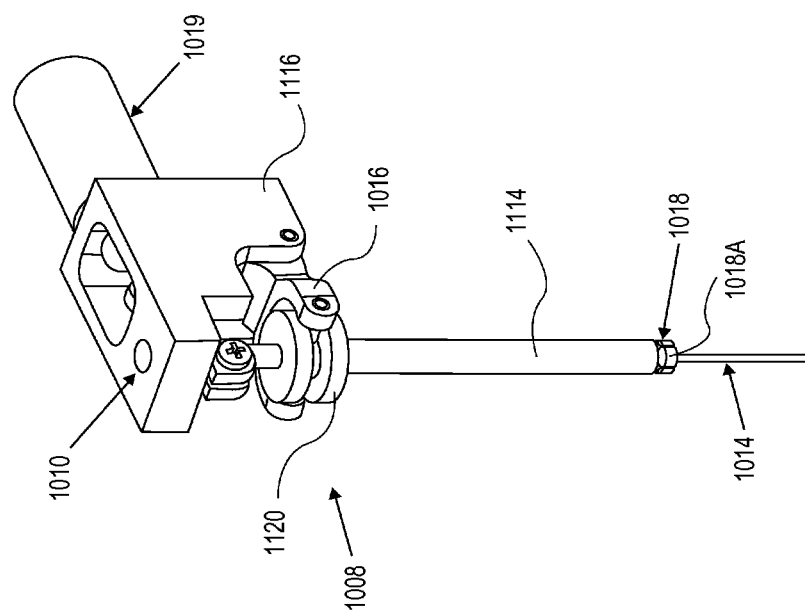
FIG. 11B
FIG. 11A

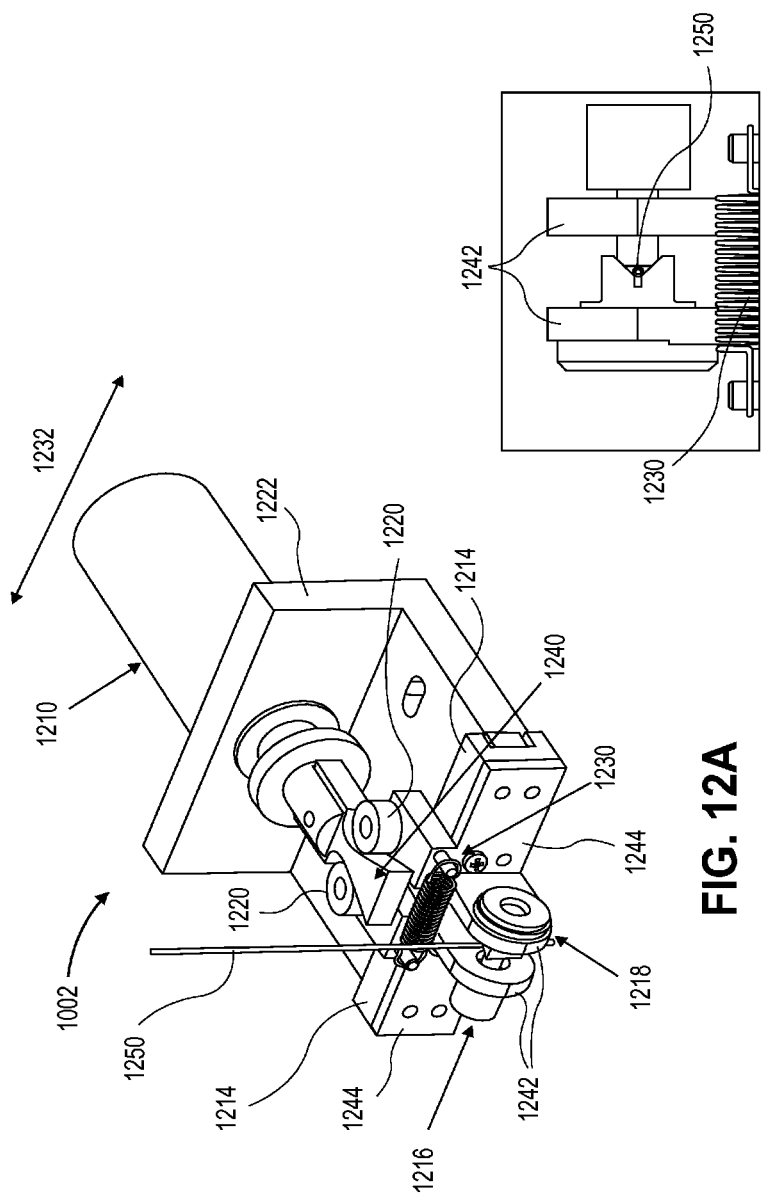

ANALYTICAL SYSTEM WITH CAPILLARY TRANSPORT

CROSS-REFERENCES TO RELATED APPLICATIONS

This application is a continuation of U.S. patent application Ser. No. 14/026,358, filed on Sep. 13, 2013, which is a non-provisional of and claims the benefit of the filing date of U.S. Provisional Application No. 61/701,360, filed on Sep. 14, 2012, both of which are herein incorporated by reference in their entirety for all purposes.

BACKGROUND

Embodiments of the invention can be directed to systems and methods that utilize capillaries to analyze samples. For example, some embodiments of the invention relate to systems and methods for accurately determining serum indices, e.g. for lipemia, hemolysis, and icterus, from serum and plasma samples in uncapped sample tubes.

Laky or chylous samples, of lipemic, hemolytic or icteric patients commonly interfere with other laboratory tests that use optical methods. Thus, for reliable sample handling automation, it is desirable to measure serum index before a sample is committed to an analyzer for testing to avoid erroneous measurements. The serum index is typically measured by sample aspiration and measurement on an analyzer instrument. For serum index to be viable in an automation device, the complete cycle time for a sample needs to match or exceed the speed of the sample throughput.

U.S. Pat. No. 5,734,468 (US '468) discloses a method and device for detecting the presence of hemolysis, icteris and lipemia in a serum sample aspirated in a transparent aspiration probe connected to a pump (see FIG. 4 of US '468). In the disclosed system, a liquid sample volume from a sample container is aspirated into the aspiration probe by applying an aspiration vacuum. The fluid sample is aspirated until the filling level in the aspiration probe reaches an optical measurement section (see FIG. 2 of US '468). At the optical measurement section, a connected fiber optics emits light into the optical transparent section and detects the transmitted part of light in a detection fiber optics at the opposite side.

A disadvantage of the disclosed system of US '468 is the need to include a washing step for the aspiration probe including the measurement section, before a subsequent sample can be measured. This reduces the throughput of the system and increases the risk of erroneous measurement results due to contamination of the subsequent sample.

U.S. Pat. No. 7,688,448 B2 (US 448) discloses an apparatus that is used to measure the serum index by a non-contact approach, emitting light through the primary sample container (see schematics in FIG. 4 of US '448). The emitted light spectra of two different light sources are combined by a beam splitter element and the combination is directed to one defined point of the primary sample container. The absorption signal is detected with a detector optic on the opposite side of the container and is recorded in a computer unit (see FIG. 18 of US '448).

A disadvantage of the disclosed apparatus of US '448 is that in the automatic processing of primary sample containers in an laboratory environment, labels may be attached to the containers. Labels can disturb or suppress the signal from the emitting optics. This makes the apparatus unable to detect a valid serum index result for a sample provided within a primary sample container.

To overcome the previously described disadvantage of measuring through a label applied to a primary sample container, US 2010/0303331 A1 (US '331) suggests using uncapped sample containers in combination with a sensor optic in a light tight measurement container. The disclosed apparatus in US '331 uses a light source below the sample container position and a camera in a moveable light tight box. When a sample is provided by a conveyor track at the measurement position, the box is lowered until it produces a light tight enclosure with the conveyor track (see FIG. 5B of US '331). The light source then emits a broad spectrum of light from below to the sample and the camera detects the transmitted signal from the sample to determine the serum index result.

A disadvantage of the disclosed apparatus in US '331 is that for previously centrifuged samples, no valid signal for serum index can be measured, since the emitted light will be almost completely blocked by the coagulum. Thus, this system is unsuitable for determining valid serum index results, based on blood serum or plasma.

Embodiments of the invention address these and other problems, individually and collectively.

BRIEF SUMMARY

Embodiments of the present invention include a device and method to overcome the previous mentioned disadvantages and enables an automatic system to measure the serum index result for a sample by aspirating the serum or plasma fraction of the sample in a disposable and optically transparent probe. The aspirated serum or plasma is then measured at an optical reading unit to determine the serum index, without disturbing label or coagulum signal attenuation. Further, the disposable is discarded and the subsequent measurement is conducted with a new, clean disposable, which eliminates the risk of cross contamination and the measurement of erroneous results.

Although serum index measurements are described in detail, embodiments of the invention are not limited thereto. Embodiments of the invention can be used to determine any suitable characteristic of any suitable sample.

One embodiment of the invention is directed to an analytical system comprising a storage container configured to store a plurality of capillaries, and a capillary orientation device. The analytical system may further comprise a gripper configured to receive at least one of the plurality of capillaries. An end of the at least one capillary is configured to contact a sample in a sample container and draw the sample in the capillary. In the system, a reader is configured to detect a signal from the sample in the capillary.

Another embodiment of the invention is directed to a method comprising loading a plurality of capillaries into a storage container, transferring a capillary in the plurality of capillaries to a gripper, contacting the capillary to a sample in a sample container and drawing the sample into the capillary, and detecting a signal from the sample in the capillary by a reader.

These and other embodiments of the invention are described in further detail below, with reference to the drawings.

BRIEF DESCRIPTION OF THE DRAWINGS

FIG. 2A shows a top perspective view of a sliding plate bulk feeder according to an embodiment of the invention.

FIG. 2B shows a bottom perspective view of a sliding plate bulk feeder according to an embodiment of the invention.

FIG. 3A shows a top perspective view of a vibrating plate bulk feeder according to an embodiment of the invention.

FIG. 3B shows a close up, side cross-sectional view of a portion of the vibrating plate bulk feeder shown in FIG. 3A.

FIG. 4 shows a top perspective view of a bulk feeder with a belt transport bridge.

FIGS. 9A-9C show a portion of a capillary rotator arm as it rotates a capillary from a horizontal orientation to a vertical orientation.

FIGS. 11A and 11B show detailed views of a capillary gripper according to an embodiment of the invention.

FIG. 12A shows a perspective view of a capillary reader according to an embodiment of the invention.

FIG. 12B shows a close up view of a clamping mechanism.

DETAILED DESCRIPTION

Figure 1A:
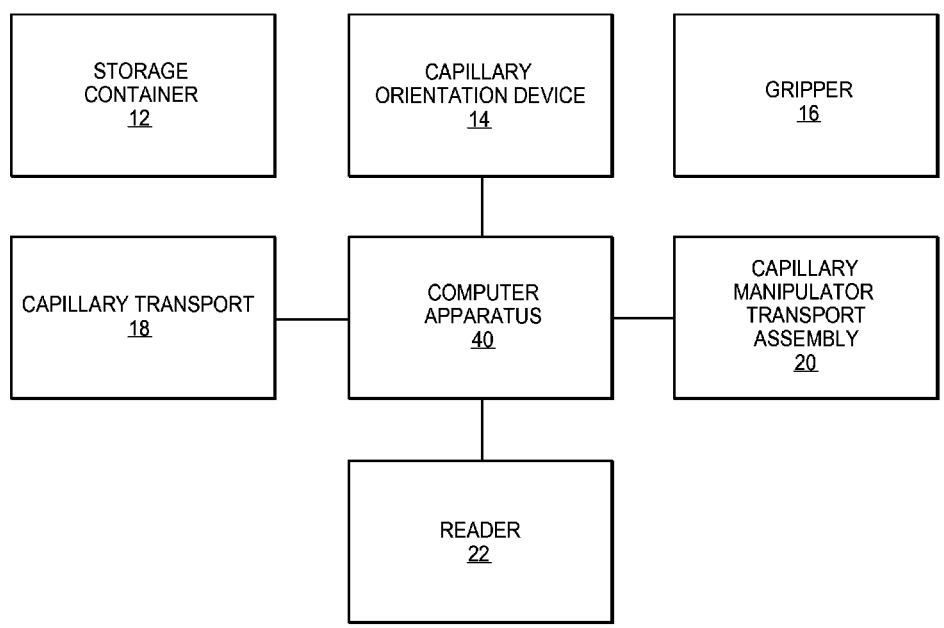
FIG. 1A shows a block diagram of some components that are used in embodiments of the invention.

Embodiments of the invention can use glass or plastic capillaries to aspirate samples and enable light absorption measurements. The capillaries can aspirate a sample in a sample container by mere contact with the surface of the sample in the sample container. No pumping action is required. After a measurement has taken place, the capillary that is used to obtain the measurement is discarded, thereby eliminating carry-over contamination issues, and satisfying the need to avoid washing.

Capillaries having different lengths and inside diameters may be used in embodiments of the invention. In some embodiments, suitable capillaries may include lengths that are greater than about 10 mm long and less than about 1000 μm inside diameter or outside diameter. For example, a suitable capillary may be about 50 mm long and may have about a 400 μm inside diameter. Other suitable capillaries may have dimension that are greater or less than these dimensions.

The system according to an embodiment of the invention operates by loading a single capillary from a capillary dispenser by means of a capillary orientation device such as a capillary loader or a capillary rotator into a gripper. Other orientation devices may include an appendage on a drop door or capillary door, alone or in combination with the capillary loader or the capillary rotator.

The gripper can be part of a capillary manipulation transport assembly, which can move the capillary over an uncapped sample tube containing a sample. It can lower the capillary until it contacts the surface of the sample in the sample tube. The sample is then immediately drawn into the capillary by surface tension and adhesion forces. Advantageously, no pumps are required in embodiments of the invention. Further, the capillaries used in embodiments of the invention are disposable, thereby speeding up the analytical process, because the capillaries are not washed. The risk of contamination is also reduced relative to conventional systems, since the capillaries need not be reused in some embodiments of the invention.

In some embodiments of the invention, a capillary reader that reads the light absorption through the capillary performs a reference scan without a capillary installed. The capillary is then moved into the reader where another scan is performed measuring the transmitted light. An absorbance is then calculated using these two scans. The light source can comprise two LEDs (420 nm and "white" spectrum) whose emission, either directly or through a fiber optic cable, is directed through a slit that allows the light to pass through the center of the capillary. The reader, with clamps closing over the capillary cylindrical surface, aligns the capillary to the slit and detection fiber cable. The refracted light is collected by the detection fiber cable and is transmitted through an optical slit onto the diffraction grating of a spectrophotometer. The reflected light from the grating can be measured with a diode array detector providing a spectral measurement from 400 to 700 nanometers.

Embodiments of the invention can advantageously be used to measure serum index values in biological samples. However, embodiments of the inventions can be used to measure values in other biological samples. For example, embodiments of the invention can be used to detect the presence or absence of a particular analyte in a biological or chemical sample.

Before discussing specific embodiments of the invention, some descriptions of some terms that are used in this application may be useful.

A "storage container" may include any suitable body that may store structures such as capillaries. A storage container may have any suitable geometry (e.g., a box-like shape) and can have at least one entry and exit for capillaries. Suitable storage containers may be constructed of any suitable material and may store greater than 50, 100 or even 1000 capillaires in some embodiments of the invention.

A "gripper" can include any suitable device configured to grip another structure such as a capillary. In some embodiments, the gripper may include a sleeve and a collet so that the gripper can at least partially protect, and transport the capillary from locations that may include, for example, a sample container with a sample and a reader that can read a signal from a sample that is within the capillary.

A "reader" may include any suitable device that can determine a characteristic of a sample. In some embodiments, the sample may be present in a capillary and the characteristic may relate to a serum index value associated with the sample. Suitable readers may include emitters (e.g., optical emitters), detectors (e.g., optical detectors), and other components (e.g., clamps, solenoids) that can facilitate the determination of a characteristic of a sample.

A "signal" may include any suitable electromagnetic impulse. In embodiments of the invention, an output signal can be produced from a sample within a capillary after the sample in the capillary receives an input signal. Suitable signals include optical signals.

FIG. 1A depicts a schematic block diagram of some components of a system according to an embodiment of the invention. The components may include a capillary storage container (or bin) 12, which may hold capillaries. The storage container 12 may be present in a capillary dispenser unit. The system may also comprise a capillary transport 18 (which may include, for example, a wheel or a conveyor) which carries individual capillaries to a capillary orientation device 14.

The capillary orientation device 14 (e.g., a loader or a rotator) may be used to supply a capillary to a gripper 16. The gripper 16 may carry a capillary, and may be manipulated by a capillary manipulator transport assembly 20, so that the capillary contacts a sample and is eventually transported to the reader 22. Each of these components is described in further detail below.

Figure 15:
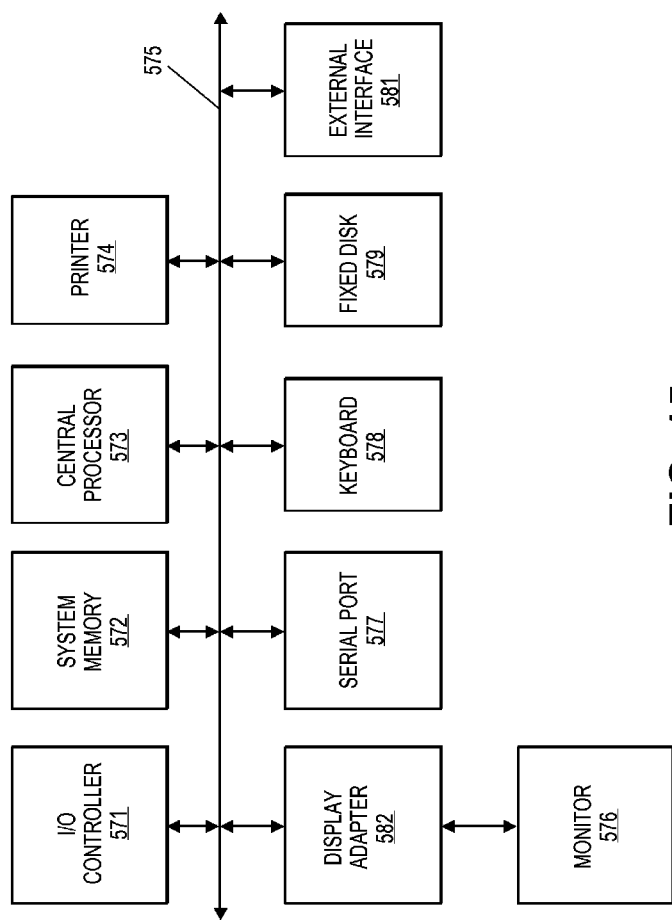
FIG. 15 shows a block diagram of a computer apparatus.

A computer apparatus 40 may control and/or receive data from the capillary transport 18, the capillary orientation device 14, the capillary manipulator transport assembly 20, and the reader 22, as described herein. Some components of an exemplary computer apparatus are shown in FIG. 15. The computer apparatus may include a computer readable medium comprising code that allows a processor to perform any of the functions described herein. Further, the computer readable medium may comprise a database of information that can be used to determine the characteristics of the samples that are being analyzed. For example, lookup tables correlating signals received from the samples being analyzed by the readers to specific sample characteristics may be present in the computer readable medium and/or the computer apparatus.

Figure 1B:
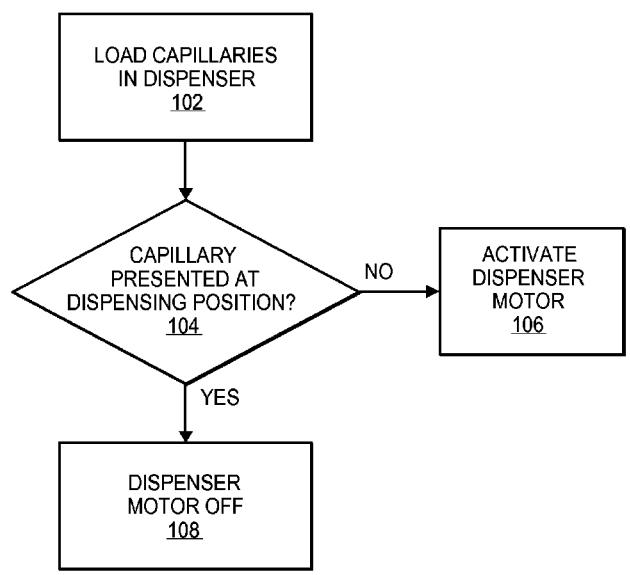
FIGS. 1B-1C show flowcharts illustrating methods according to an embodiment of the invention.
Figure 1C:
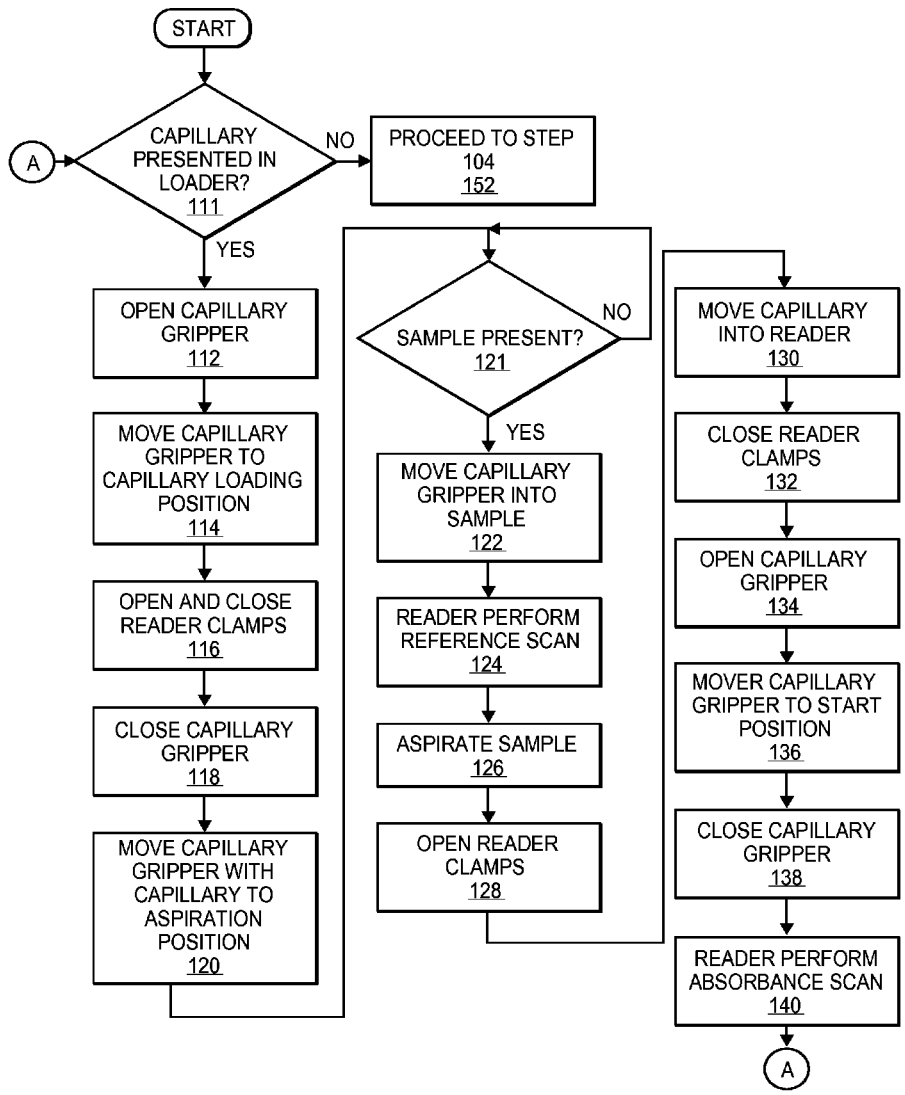

FIGS. 1B and 1C depicts an exemplary workflow for a capillary manipulation and serum index measurement process according to an embodiment of the invention. It is noted that embodiments of the invention are not limited to the particular number or order of steps shown in FIGS. 1B and 1C, and that other embodiments of the invention may include more or less steps. It is also understood that further details regarding each of the steps are described with respect to the specific components on the overall system and any of those details may be incorporated into the steps below without departing from the scope of the invention.

Referring to FIG. 1B, at step 102, capillaries are loaded into a storage container of a capillary dispenser unit. Various examples of capillary dispenser units are provided below. The capillaries may be loaded into the storage container by hand, or may be loaded automatically by an external machine.

In step 104, a sensor detects whether a capillary is present at a dispensing position in the capillary dispenser unit. As will be shown in the various capillary dispenser unit embodiments below, one capillary may be dispensed at a time from the capillary dispenser unit.

In step 106, if the capillary is not in the dispensing position in the capillary dispensing unit, then a dispenser motor in the capillary dispensing unit is activated and the capillary is dispensed to a loader. In step 108, if the capillary is in the dispensing position, then the dispenser motor in the capillary dispensing unit is turned off.

Figure 8:
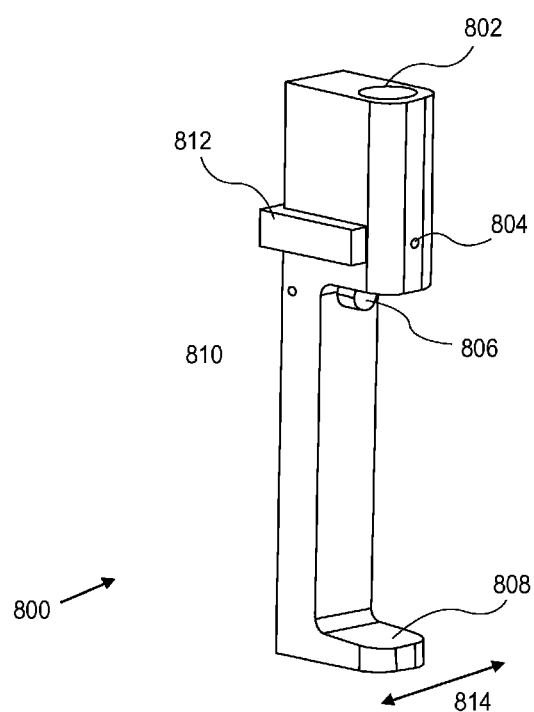
FIG. 8 shows a perspective view of a capillary loader according to an embodiment of the invention.

Referring now to FIG. 1C, in step 111, a determination is made as to whether or not a capillary is present in the loader. An exemplary loader is shown in FIG. 8 and is described in further detail below. If a capillary is in the loader, then a capillary gripper is opened (step 112), and the capillary gripper is moved to a capillary loading position (step 114). An example of a capillary gripper is shown in FIG. 11A and is described in further detail below. If a capillary is not in the loader, then the process may proceed back to step 104 in FIG. 1B (step 152). The motor in the capillary dispensing unit may be activated to ensure that a single capillary is present at a dispensing position and is present in the loader.

In step 116, a reader clamp is then opened and closed (step 116). Exemplary reader clamps are shown in FIGS. 12B and 13C. In this step, the reader releases any capillary disposed therein to waste from the prior test. It is done at this time because of the dwell period for the capillary to load into the gripper. This step can be accomplished without any increase in cycle time.

In step 118, the capillary gripper is then closed (step 118). This can be done to ensure that the capillary is secured to the capillary gripper and can be transported to an aspiration position where a sample tube containing a sample to be analyzed is located.

In step 120, the capillary gripper and the capillary are moved to an aspiration position. As will be described in further detail below, the capillary gripper can be moved using a capillary manipulator transport assembly that includes a transporting arm. The transporting arm may be capable of moving in X, Z, and/or Z directions to transport the gripper and the capillary to the desired location.

In step 121, a cue from the automation control system is sent to the serum index control system when a sample tube is present. In step 122, if the sample tube is present, then the capillary gripper is moved so that the capillary contacts the sample. A reference scan (step 124) is then performed by the reader prior to reading any signals from the sample to be analyzed. In step 126, the sample is aspirated into the capillary after the capillary contacts the sample in the sample tube.

In step 128, the reader clamps in the reader are then opened. The capillary gripper is then moved by the transporting arm so that the capillary is in the reader clamps (step 130) and can be read by the reader. In step 132, the reader clamps are then closed. The capillary gripper is then opened (step 134), thereby releasing the capillary. The capillary gripper is then moved away from the reader to a start position (step 136). In step 138, the capillary gripper is then returned to a closed configuration.

In step 140, an absorbance scan is then performed (step 140) on the sample in the capillary, while the capillary is within the reader. A computer apparatus may then analyze the output signal from the sample and may characterize the sample. After the scan is completed, the reader clamps can be opened and the capillary drop into a waste container situated below the reader clamps.

Further details regarding the components in the system are provided below.

I. Capillary Dispenser Units

A. Sliding Plate Bulk Feeder

FIGS. 2A and 2B depict an embodiment of the capillary dispenser unit 200 where the capillaries are stored in horizontal orientations in a storage container 204. The storage container 204 may alternatively be referred to as a capillary reservoir (or bin) in some embodiments. In this embodiment, the storage container 204 is limited on the bottom side by a sliding plate (or tray) 218 coupled to and parallel with a planar deck 202.

The sliding plate 218 comprises a small linear cavity suitable to accommodate a single capillary. A capillary drop door 210 is coupled to the sliding plate 218 by a hinge (not shown) and allows the capillary drop door 210 to pivot upward and downward. When the capillary drop door 210 is in a downward position, the capillary in the small linear cavity can roll down the top major surface 210A of the capillary drop door 210. As it rolls down the top major surface 210A of the capillary drop door 210, one end of the capillary may contact an appendage 210B that protrudes upward from the top major surface 210A of the capillary drop door 210.

This has the effect of impeding the movement of one end of the capillary as it rolls down the top major surface 210A while the other end continues to roll down the top major surface 210A. The capillary then rotates so that it can be oriented with and enter an aperture in a capillary loader (described in detail below).

In this embodiment, two parallel linear slides 208 are attached to a bottom surface of the planar deck 202. The sliding plate 218 is guided by grooves in the two parallel linear slides 208, which are cooperatively structured with the lateral sides of the sliding plate 218.

A linear crossbar 216, which may include a main crossbar body 216A and a protrusion 210B extending upward from the main crossbar body 216A. The linear crossbar 216 can be attached to the middle portions of the parallel linear slides 208 and can be oriented perpendicular to the orientations of the linear slides 208. The linear crossbar 216 may also be stationary and can restrict the movement of the capillary drop door 210.

The protrusion 216A may contact a bottom surface of the capillary drop door 210. When the sliding tray 218 and the capillary drop door 210 move away from the depicted drive motor 214 and the protrusion 216B approaches the hinge which attaches the capillary drop door 210 to the sliding tray 218, the capillary drop door 210 is free to move downward as shown in FIG. 2B. With the assistance of gravitational forces, this allows a capillary to roll down the top major surface 210A as described above.

As shown in FIG. 2B, a drive motor 214 and a crank assembly 212 may be attached to a bottom surface of the planar deck 202. They may be operatively coupled to the sliding tray 218 to move the sliding tray 218 forward and backward.

The storage container 204 can be of any suitable configuration or size. In this example, the storage container 204 can be formed by two opposing walls 204A and two parallel walls 204B oriented perpendicularly with respect to the end structures 204A. The parallel walls 204B may be spaced at a distance that is slightly longer than the lengths of the capillaries that are stored in the storage container 204. The opposing walls 204A have downwardly sloped inner surfaces 204A-1 to allow the capillaries stored therein to funnel down to a small cavity in the planar deck 202 and a cavity in the sliding tray 218 by gravity.

The capillary dispensing unit 200 can start and stop with a signal from a capillary loader, which is described in further detail below). In operation, a vibrator (not shown) can facilitate the capillary orientation within the storage container 204. A single capillary is deposited within a slot in the sliding tray 218 as the sliding tray 218 moves along the bottom of the planar deck 202. The sliding tray 218 moves away from the drive motor 214 thereby allowing the capillary drop door 210 to open. The appendage 210A on the capillary drop door 210 imparts a rotation on the capillary as it rolls down the door to move it to a vertical orientation and into the capillary loader (described in further detail below).

One advantage of the capillary dispenser unit 200 embodiment shown in FIGS. 2A and 2B is that the capillary reservoir and the capillary loader (not shown in FIGS. 2A and 2B) can be close to each other. This provides for a more compact system and improves the accuracy of transferring capillaries from the capillary dispenser unit 200 to the capillary loader. Further, the capillary dispenser unit 200 can accurately and reliably dispense one capillary at a time to the capillary loader.

B. Vibrating Plate Bulk Feeder

FIG. 3A depicts another embodiment of a capillary dispenser 300. The capillary dispenser 300 in this embodiment includes an inclined surface on the bottom.

The capillary dispenser 300 comprises a storage container 318, which can be formed in part by opposing walls 304A, and two parallel walls 304B perpendicular to the opposing walls 304A. The storage container 318 can store a plurality of capillaries (not shown). The distance between the two opposing walls 304A may be slightly greater than the lengths of the capillaries that will be stored in the storage container 318.

A frame 338 is attached to one of the parallel walls 304B. The frame 338 supports a drive motor 312 which moves an actuator cam 314. A capillary stop lift bearing 310 and a spring 324 are also present. A capillary stop 322 is present to meter the number of capillaries that will exit the storage container 318. The capillary stop 322 can be in the form of a vertical plate-like structure that has an end that is positioned proximate the lowest point of the storage container 318.

As shown in FIG. 3B, a bottom plate 302 with an inclined surface can be work in conjunction with the capillary drop lever 320. The bottom surface of the capillary stop 322 is also slanted downward so that the bottom surface of the capillary stop 322 and the inclined surface of the bottom plate 302 are substantially parallel.

As shown, when the capillary stop 322 is biased upward, a space between the upper surface of the bottom plate 302 and a bottom surface of the capillary stop 322 is slightly larger than the outer diameters of the capillaries between them. When the capillary stop 322 is down, the capillary stop 322 and the bottom plate 302 can sandwich the capillaries 50 so that they cannot move. One capillary 50A may not be sandwiched between the capillary stop 322 and the bottom plate 302. When the drop lever 320 is actuated by moving downward, the single capillary 50A may be released. This process is further described below with respect to FIGS. 3C and 3D.

During operation, a vibrator (not shown) facilitates capillary orientation within the storage volume of the storage container 318. Further, the motor 312 attached to the actuator cam 314 alternately actuates the capillary stop 322 and the capillary drop lever 320. When the capillary drop lever 320 is closed by a spring force (spring not shown in FIG. 3B) and the capillary stop 322 is lifted, the capillaries 50, 50A roll down the inclined surface toward the capillary drop lever 320. A drop lever bearing 316 may be coupled to the actuator cam 314, and the drop lever bearing 315 may actuate the capillary drop lever 320. When the capillary stop 322 is lowered by spring force from spring 324, the capillary drop lever 320 is opened allowing one capillary to drop. The capillaries under the capillary stop 322 are thus prevented from moving. Also, in this embodiment, an appendage (not shown) on the bottom plate 302 can impart a rotation on the capillary, as falls by gravity to a vertical orientation and into the capillary loader (described in further detail below).

Figure 3C:
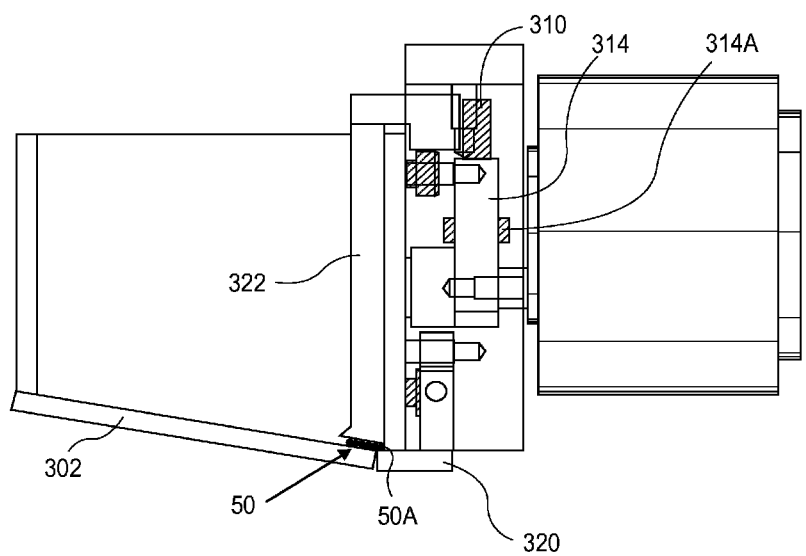
FIG. 3C shows a cross-sectional side view of the feeder shown in FIG. 3(a) where a capillary drop lever is in a closed position in a capillary stop is in a raised position.

FIG. 3C shows a cross-sectional side view of the capillary dispenser unit shown in FIG. 3A where a capillary drop lever 320 is in a closed position and the capillary stop 322 is in a raised position. In this state, the capillaries 50, 50A are free to roll down the inclined bottom plate 302 towards a lower end of the bottom plate 302 towards the capillary door 320. The actuator cam 314 pushes up on the capillary stop lift bearing 310, against the compression force of the spring (see element 324 in FIG. 3) so that the capillary stop 322 is lifted upward and does not contact the capillaries 50, 50A. The capillary door 320 is closed in FIG. 3C.

Figure 3D:
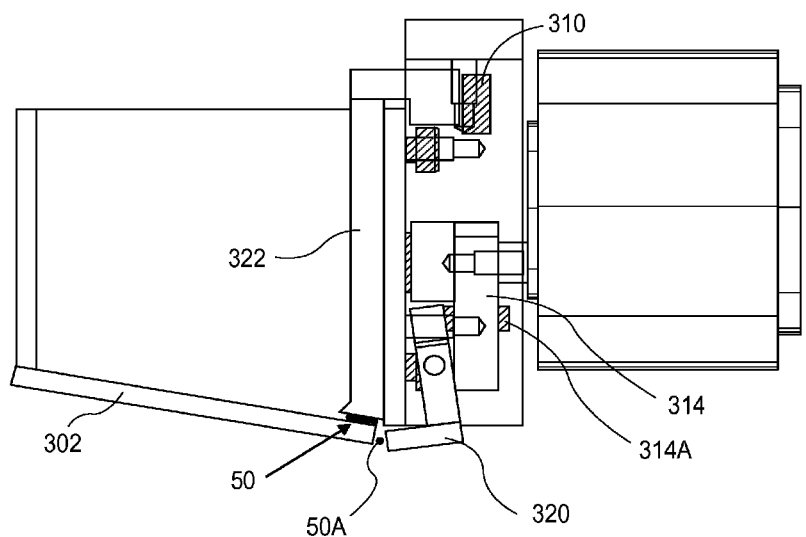
FIG. 3D shows a cross-sectional side view of the feeder shown in FIG. 3(a) where a capillary drop lever is in an option position in a capillary stop is in a lowered position.

FIG. 3D shows a cross-sectional side view of the capillary dispenser unit shown in FIG. 3A where a capillary drop lever 320 is in an open position and the capillary stop 322 is in a lowered position. In this state, the capillaries 50 are restrained from rolling, due to downward pressure from the capillary stop 322. However, the single capillary 50A may be released as it is not constrained by the downward pressure of the capillary stop 322. To open the capillary drop lever 320, the actuator cam 314 has a contacting portion 314A, which contacts a drop lever bearing coupled to the drop lever 320. This motion causes the bottom portion of the drop lever 320 to pivot to the right in FIG. 3D, thereby allowing the capillary 50A to be released.

The advantage of the capillary dispenser unit embodiment shown in FIGS. 3A-3D is also the close distance between capillary reservoir and the capillary loader. This embodiment is also less damaging to the sensitive capillaries, so that the number of broken capillaries, and thus the number of jam situations in the capillary loader can be reduced.

C. Bulk Feeder with Capillary Transport

FIG. 4 depicts an embodiment of a capillary dispenser unit 400 including a capillary transport unit. In this embodiment, the capillaries are stored in capillary storage container 406 with an inclined surface on at least one side. The capillary transport unit comprises a toothed transport belt arrangement, where one or more transport belts 414, each with grooves, is suited to accommodate a single capillary 50 per groove. A gear driven stepper motor 415 may be used to drive the belt 414.

The toothed belt 414 can be applied to the inclined side of the capillary storage container 406 transporting capillaries to the top of the capillary storage container 406. A capillary stripper element 418 is arranged near a top area of the capillary storage container 406 to allow only one capillary per groove to exit the capillary storage container 406. At the top of the capillary storage container 406, each capillary is passed to a conveyor 404 on a transport bridge 412. In one embodiment of this transport bridge 404, an opening between the two lane transport tooth belt is provided, to allow broken capillaries to fall down into a waste container (not shown) underneath the opening of the transport bridge 404. The transport bridge 404 may be formed by a number of columns 412A that are perpendicular to a horizontal base 410 and a horizontal platform 412B. A capillary lifter and rotator assembly 408 can be at the opposite end of the bridge 412 as the capillary storage container 406. A Y-Z crane assembly 402 can be on top of the capillary lifter and rotator assembly 408. A distal end of the crane assembly 402 may contain a rotating arm that can manipulate a capillary to a reader 405.

Figure 5:
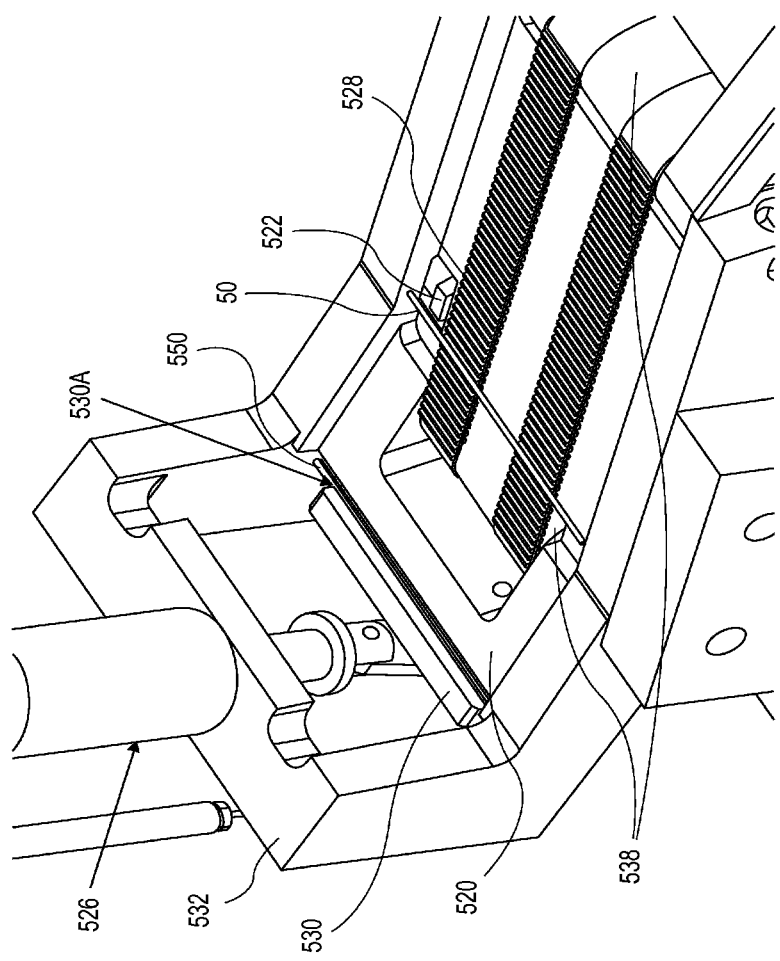
FIG. 5 shows a top perspective view of a loading ramp and capillary rotator.

FIG. 5 shows the loading ramp end of the transport bridge 412. The capillary 550 is passed to the loading ramp tooth belt 528 transporting the capillary 550 to a capillary lift surface 520 with an approximately 5 degree slope. Other slope values are possible in other embodiments of the invention. The capillary 550 is lifted from the groove of the loading ramp tooth belt 528 that is moved by rollers 538 and subsequently slides downwards on the capillary lift surface 520 into a cavity 530A of a capillary rotator 530, which can be driven by a rotator solenoid 526 attached to a frame 532. The capillary rotator 530 rotates (e.g., clockwise) the capillary 550 to a vertical position to provide a single capillary 550 to the capillary manipulator transport assembly.

During the operation of the transport arrangement, a sensor element 522 near the capillary lift surface 520 detects the presence of a capillary on the loading ramp tooth belt 528 and in response to the capillary rotator availability, it controls the tooth belt transport arrangement such that single capillaries are released to the capillary lift surface 520 if the capillary rotator 530 is in horizontal position.

One advantage of this embodiment is the flexibility in the positioning of capillary storage container (e.g., the hopper) and the capillary rotator. The transport arrangement can be adapted to the requirement of the surrounding system. Further, an automatic capillary disposal function avoids the loading of broken capillaries into the capillary rotator and thus avoids malfunctions in the serum index measurement system.

Figure 6:
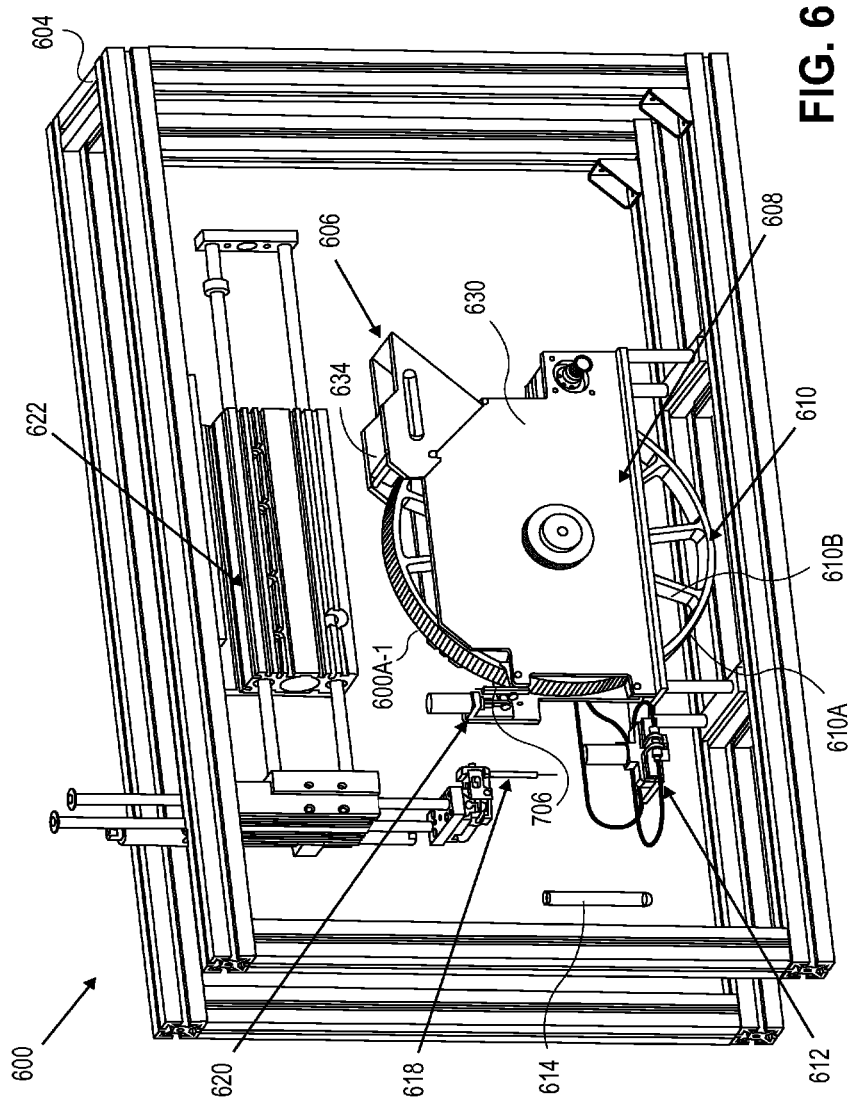
FIG. 6 shows a perspective view of a bulk feeder with a wheel transport.

FIG. 6 depicts another embodiment of a capillary dispenser unit 600. The capillary dispenser unit 600 comprises a slotted wheel transport unit 608 that rotates on the wheel frame 630 to transport capillaries between the capillary storage container 606 (e.g., a capillary hopper) and the capillary rotator 706. The toothed wheel 610 comprises spokes 610B which support a circular rim 610A comprising multiple grooves 600A-1 suited to accommodate a single capillary per groove.

The slotted wheel 610 enters the capillary storage container 606 on its inclined side and transports capillaries by rotation of the wheel 610 in an upwards direction to the top portion of the storage container 606. A stripper element 634 is arranged on the top portion of the storage container 606 to allow only one capillary 50 per groove to exit the storage container 606 and to be further transported to the capillary rotator 706 (see FIGS. 6 and 7). With reference to both FIGS. 6 and 7, the capillary 50 is lifted from the groove of the toothed wheel 610 by a capillary lift surface formed by parallel capillary guides 702. The capillary 50 then slides down the capillary guides 702 into the cavity of the capillary rotator 706, which can be present in a capillary loader 620.

FIG. 6 also shows a read head assembly 612 (or reader), a capillary gripper 618, and a sample tube 614. A linear servo drive 622 may manipulate a transport assembly which may move the capillary gripper 618.

Figure 7:
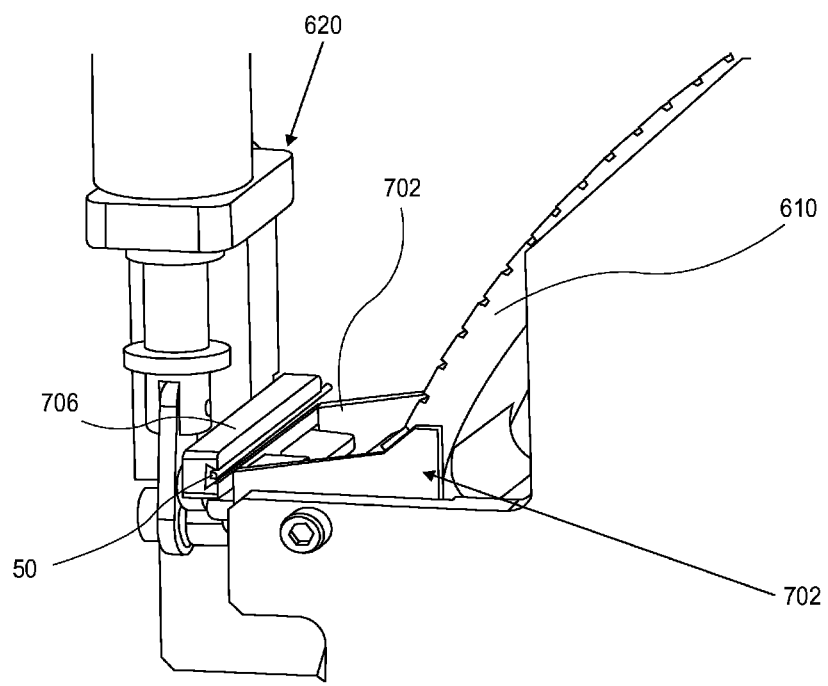
FIG. 7 shows a close up perspective view of a bulk feeder with a wheel transport.

Referring to FIG. 7, if a broken capillary is transported by the toothed wheel 610 to the capillary guides 702, the broken capillary will directly fall downwards through an opening between the guides into a waste container (not shown). The capillary rotator 705 rotates the capillary 50 in vertical position to provide a single capillary 50 to the capillary manipulator transport assembly.

During operation, a sensor element (not shown in FIG. 7) near the capillary guides 702 detects the presence of a capillary on the slotted wheel 610. In response to the capillary rotator 706 availability, the sensor element controls the slotted wheel transport arrangement such that a single capillary is released to the capillary lift surface if the rotator 706 is in a horizontal position.

One advantage of the embodiment illustrated in FIGS. 6-7 is also the flexibility in the positioning of storage container and the capillary rotator by adjusting the wheel diameter (however, the transport distance may not be as flexibly adjustable as in the transport bridge embodiment). The loading of the storage container with a volume of capillaries can be either achieved by direct access to the storage container or by a storage container loading mechanism. The capillary storage container loading mechanism may be, for instance, an additional container that can be pre-loaded with a volume of capillaries and is moveable to the storage container on a sliding transport system. In operation, if the storage container loading mechanism is in close contact with the storage container (preferably positioned above the open storage container), then the pre-loaded capillaries can be released from the storage container loading mechanism to the storage container volume.

An additional advantage of this embodiment is that the transport of capillaries between the storage container and the rotator can occur without the need for synchronization of multiple transport belts by a complex pulley arrangement. Also, in this system, the broken capillary disposal function avoids the loading of broken capillaries into the capillary loader and thus avoids malfunctions in the serum index measurement system.

In this and in other embodiments of the invention, the bulk loading of the capillary storage container can be accomplished by prepackaging capillaries within a disposable package of capillaries. The package can be placed in the storage container, and then a retaining flap can be removed or a door can be opened on the package bottom. This allows the capillaries to empty from the package bottom and into the storage container as it is lifted from the storage container.

II. Capillary Loaders and Rotators

A. Capillary Loader

FIG. 8 depicts one embodiment for a capillary loader 800 that receives a vertical oriented capillary from one of the previously described capillary dispenser units and provides the capillary to the capillary manipulator transport assembly. The capillary loader 800 can be used with the dispenser unit embodiments shown in FIGS. 2 and 3 above, and can receive individual capillaries from them.

In embodiments of the invention, the capillary is provided from the capillary dispenser unit in a vertical position and enters the capillary loader 800 through an inlet funnel 802. A capillary detector in the capillary loader 800 uses an LED and a photodiode sensor 812 to sense the presence of a capillary in the loader 800. A light beam can enter a portion of an elongated housing 810 and exit through a beam dump 804. The presence of a capillary will create a reflection of the light beam from the outer wall of the capillary onto the photodiode sensor. The housing 810 can have somewhat of a "C" shape, where the inner portion of the "C" shape can receive a capillary manipulator transport assembly.

Figure 10:
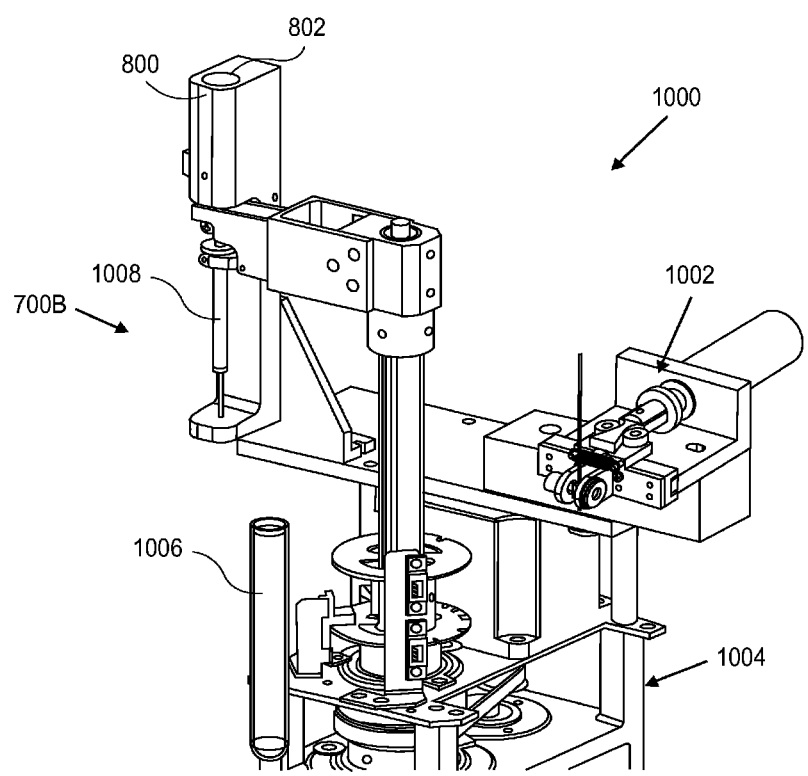
FIG. 10 shows a perspective view of a capillary manipulator transport assembly according to an embodiment of the invention.

In operation, the capillary manipulator transport assembly (not shown in FIG. 8) actuates a release button 806 allowing the capillary that is in the inlet funnel 802 to drop by gravity into the capillary manipulator transport (e.g., the gripper 1008 in FIGS. 10-11). An inclined top surface 808 at the base of the capillary loader 800 indexes the capillary extension from the capillary manipulator transport collet and allows the capillary manipulator transport to move outward without elevating beforehand. To reduce rebounding effects of a capillary from the inclined surface, a damper (not shown) can be added. An adjustment direction 814 is also shown in FIG. 8.

B. Capillary Rotator

FIGS. 9A-9C depict another embodiment for a capillary loader/rotator that receives a horizontally oriented capillary from one of the previously described capillary dispenser units and provides the capillary to a gripper (or capillary manipulator transport assembly).

In FIG. 9A, the capillary 50 is transported by the wheel 610 from the capillary storage container to the capillary rotator 706. In response to a signal from a capillary sensor (not shown) near the capillary guides 702, the capillary 50 is transported to the capillary guides 702 and slides along a capillary lift surfaces 702A of the capillary guides 702 into the cavity of the capillary rotator 706. The capillary rotator 706 is positioned horizontally in FIG. 9A.

In FIG. 9B, the capillary rotator 706 is moved by a rotator arm from a horizontal position to a vertical position to release the capillary 50. The capillary 50 slides into the gripper 1008, aligned with the rotator cavity at the release position.

In FIG. 9C, the capillary 50 has been completely transferred from the capillary rotator 706 to the gripper 1008. An inclined top surface 1070 at the base of the capillary loader indexes the capillary extension from the capillary manipulator transport collet in the gripper 1008 and allows the gripper 1008 to move outward without elevating it beforehand. To reduce rebounding effects of a capillary 50 from the inclined surface, a damper can be added.

III. Capillary Manipulator Transport (Gripper)

FIG. 10 shows a subsystem 1000 comprising a capillary loader 800, and a gripper 1008 working in conjunction with the capillary loader 800. The subsystem 1000 further comprises a sample tube 1006, a crane 1004, and a read head assembly 1002 that can be manipulated by the crane 1004. The components of the subsystem 1000 transports a capillary by rotation, and up and down movement from a capillary loading position to an aspiration position, and then to a reading position.

Referring to FIG. 11A, the gripper (alternatively referred to as a "capillary gripper" or "capillary manipulator transport") 1008 comprises a base structure 1116 that comprises a capillary loading port 1010 and is coupled to and supports a linear release sleeve 1114. While the release sleeve 1014 may have any suitable dimensions, it may have a diameter of about 4.8 mm in some embodiments of the invention. A collet 1018 is internally concentric with the release sleeve 1114 and is fastened to a base structure 1116 by the clamp at a screw location, while a disk structure 1120 is at the other end of the release sleeve 1114. A release lever 1016 is coupled to the disk structure 1120. The release lever 1016 pivots on the base structure 1116 and is rotated by the retraction of the solenoid actuator 1019. The rotation of the release lever 1016 pulls the release sleeve 1114 upwards. The upward position of the release sleeve 1114 provides clearance for the collet fingers 1018A allowing the fingers 1018A to spring open allowing clearance for capillary 1014. A solenoid actuator 1018 may be located proximate the base structure 1116. Other gripper embodiments may comprise fewer or more parts than the combination of parts shown in FIG. 10. For example, other gripper embodiments could include only the described release sleeve 1114 and collet 1018.

During operation, the empty capillary gripper 1008 is aligned with the capillary loader 800 (or rotator as previously described), allowing the capillary to drop by gravity through a capillary loading port 1010 into the gripper funnel. The loaded capillary 1014 is clamped in the gripper 1008 for transport using a collet type clamp 1018, similar to an architect's drafting pencil as shown in FIG. 11A. For sample aspiration, the gripper 1008 is first rotated in a horizontal direction over the uncapped sample tube 1020 and lowered to an aspiration position in which the lower open end of the capillary 1014 has physical contact with the fluid sample (see FIG. 11B). The sample aspiration is performed with the capillary 1014 retained within the gripper 1008. In one embodiment, the sample is drawn into the capillary 1008 by surface tension and adhesion forces. Alternatively a temporary connection of a vacuum source to the upper open end of the capillary 1008 can be applied to increase the aspiration speed and volume.

After aspiration of sample fluid, the gripper 1008 can be elevated again over the uncapped sample tube 1020 and rotated in a horizontal direction to a capillary reader at a reading position. At this position, the reader clamps the capillary by its own clamping mechanism (as described below), while the capillary 1014 is released from the capillary gripper 1008 by opening the collet 1018 using a solenoid actuator 1019 with a spring return.

IV. Capillary Reader

FIGS. 12A-12B and 13A-13C depict embodiments for a capillary reading unit comprising a clamping mechanism for a capillary and a reading head to conduct an optical measurement to determine the serum index of a liquid sample in the capillary.

FIG. 12A shows a capillary reading unit 1002 (alternatively a "reader") comprising a base structure 1222 and a solenoid actuator 1210 coupled to the base structure 1222. The solenoid actuator 1210 is coupled to a linear cam 1240 that is positioned between two roller bearings 1220. Translating arms 1244 can be move laterally in an adjustment direction 1232, and can be connected to the two roller bearings 1220, as well as a linear slide 1214. Two clamps 1242 may be coupled to the arms 1244, and they can respectively include a detection fiber fitting 1216 and an aperture 1218 for receiving light from a light source (not shown). A capillary 1250 may be disposed between the clamps 1242.

In operation, the translating arms 1244 of the clamping mechanism with clamps 1242 open by activating a solenoid 1210 to activate a linear roller slide mechanism. The mechanism may comprise a linear cam 1240 which is driven by the solenoid 1210. The linear cam 1240 can separate roller bearings 1220 1214, which can push apart the translating arms 1242 in an adjustment direction 1232. The translating arms 1244 may close by a spring force provided by a spring 1230 clamping the capillary 1250 in "V" feature of aperture (see FIG. 12B). A clearance within the clamps 1242 provided by the translating arms 1244 in the actuator mechanism provides a clamping action that self-aligns the capillary 1250. The clamps 1242 provided by the translating arms 1244 can open to release the capillary 1250 after measuring the serum index, which drops then by gravity into a waste container (not shown). Within the clamps 1242 provided by the translating arms 1244, a emitting (not shown) and detection fiber optic is positioned in a centric bore-hole for each clamp. Light emitted from the emitting fiber passes through a slit in an aperture 1218. The emitted light may comprise light with a single or different wavelengths. The aperture is comprised of a 100 micrometer by 800 micrometer slit (depending on the capillary internal dimensions) whereby the long dimension of the slit is oriented along the axis of the capillary. A detection fiber fitting 1216 and an aperture 1218 are also shown and receive a signal from the sample in the capillary 1250 that is held between the clamps 1242.

This signal can then be received by an appropriate optical detector, which in conjunction with a computer apparatus, can determine one or more absorbences at one or more predetermined wavelengths. As known by those of ordinary skill in the art, the computer apparatus can estimate the serum indices using the determined absorbences.

Figure 13B:
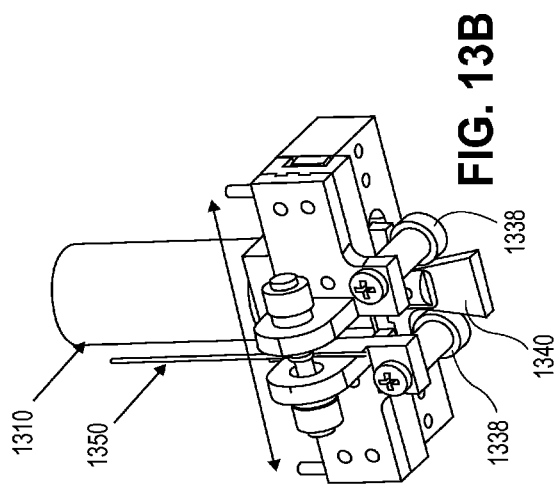
FIG. 13B shows a front bottom perspective view of a capillary reader according to an embodiment of the invention.
Figure 13C:
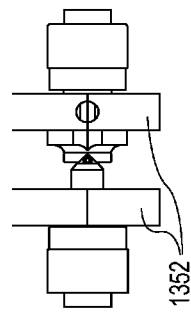
FIG. 13C shows a portion of a capillary reader according to an embodiment of the invention.
Figure 13A:
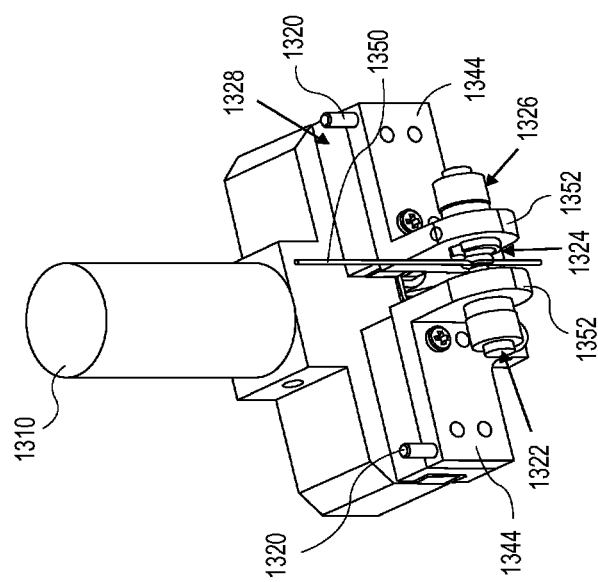
FIG. 13A shows a front top perspective view of a capillary reader according to an embodiment of the invention.

FIGS. 13A-13C show another reader according to an embodiment of the invention.

FIG. 13A shows a top, perspective view of the reader. The reader comprises a solenoid 1310 that is coupled to a base structure 1336. Linear slides 1328 are coupled to the base structure 1336, and the linear slides are coupled to translating arms 1344. Each translating arm 1344 has a return spring post 1320 extending upward from it. A spring (not shown) may be attached to the return spring posts 1320 so that the translating arms 1344 are biased towards each other in the absence of outward pressure. A detection fiber fitting 1322 and an excitation fiber fitting 1326 are coupled to the translating arms 1344.

FIG. 13B shows a bottom, perspective view of the reader. As shown in FIG. 13A, a linear cam 1340 can be driven up and down by the solenoid actuator 1310. With the aid of roller bearings 1338, the linear cam 1340 can then push the linear slides 1328 and the translating arms 1344 apart as the linear cam 1340 moves upward. When the linear cam 1340 moves (e.g. downward), a spring (not shown) attached to the spring posts 1320 can pull the translating arms 1344 together so that a capillary 1350 can be secured between the clamps 1352 attached to the translating arms 1344. This is also shown in FIG. 13C.

Referring to FIGS. 13A and 13B, in operation, the translating arms 1344 of the clamping device (including clamps 1352) open by activating a solenoid 1310 to activate a linear roller slide device. The linear slide device may comprise a linear cam 1340 which is vertically driven by the solenoid 1310. The linear cam 1340 can separate roller bearings 1338, which can push apart the translating arms 1344 on a linear slide 1328. The translating arms 1344 may close by use of a return spring (not shown) attached to the post 1320 on each translating arm 1344. A clearance within the clamps provided by the translating arms 1344 in the actuator mechanism provides a clamping action that self-aligns the capillary 1350. The clamps 1352 provided by the translating arms 1244 can open to release the capillary 1350 after measuring the serum index, which drops then by gravity into a waste container (not shown). Within the clamps 1352 provided by the translating arms 1344, a emitting and a detection fiber optic is positioned in a centric bore-hole for each clamp 1352. The emitting and detection fiber optics may be respectively disposed in excitation and detection fiber fittings 1326, 1322, respectively. As in the prior example, light emitted from the emitting fiber passes through a slit in an aperture 1324.

The aperture is comprised of a 100 micrometer by 800 micrometer slit (depending on the capillary internal dimensions) whereby the long dimension of the slit is oriented along the axis of the capillary. An excitation aperture 1324 is also shown in FIG. 13A.

The signal from the sample in the capillary 1350 can then be received by an appropriate optical detector, which in conjunction with a computer apparatus, can determine one or more absorbences at one or more predetermined wavelengths. As known by those of ordinary skill in the art, the computer apparatus can estimate the serum indices using the determined absorbences.

V. Serum Index Measurement

Figure 14:
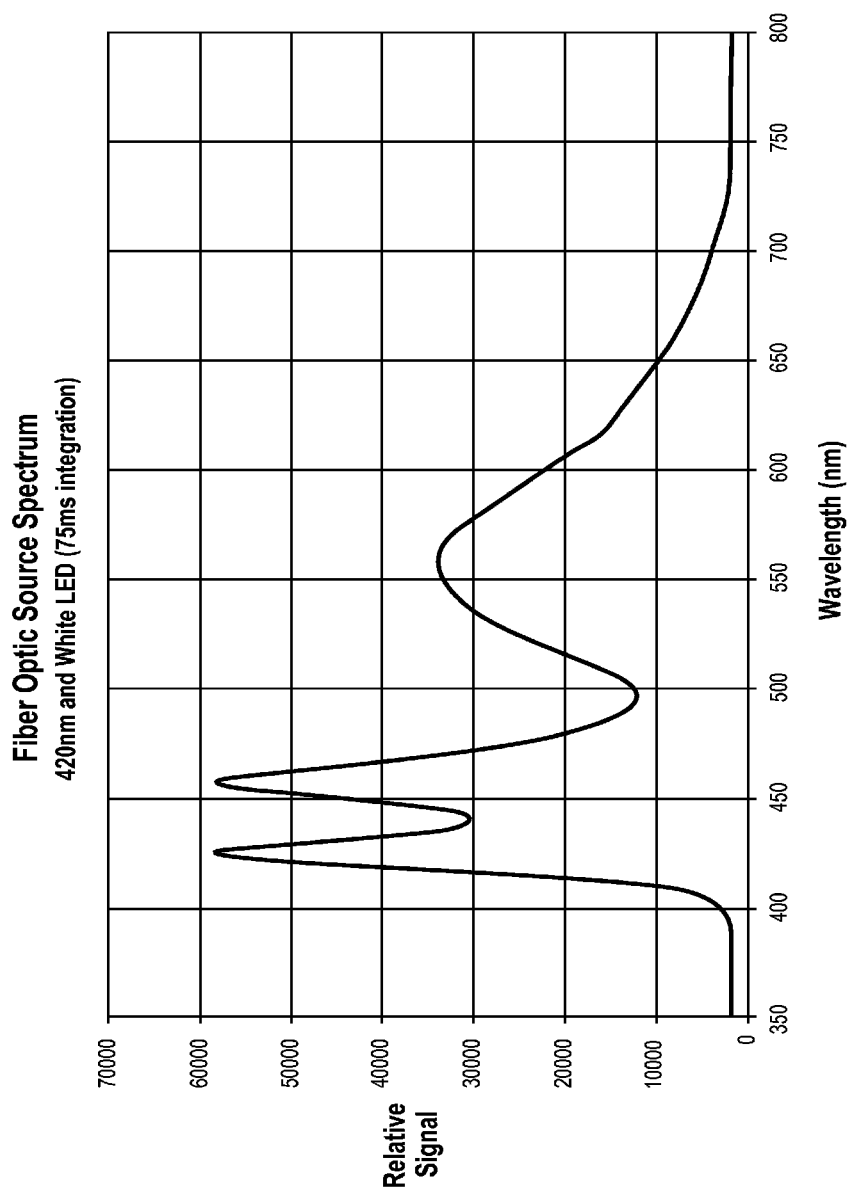
FIG. 14 shows a graph of a relative signal vs. wavelength.

FIG. 14 depicts the combined emitted spectrum of the 420 nm and white LED detected by the detection fiber optics. Other combinations of LEDs can also work for this purpose.

Before each sample measurement, a reference scan is performed without a capillary to determine a reference spectrum signal in air. A transmittance spectrum signal is measured from the next sample read. Absorbance values are calculated using the reference and transmittance scans for multiple wavelengths. Hemoglobin, icteric and lypemia indices are calculated using a specialized mathematical algorithm. It is possible to collecting a signal from each wavelength from 400 to 700 nm. However, any number of wavelengths within this spectrum will work with an appropriate mathematical algorithm.

VI. Computer Apparatus Subcomponents

FIG. 15 is a block diagram of elements that may be present in a computing device or system configured to execute a method or operation in accordance with some embodiments of the invention. The subsystems shown in FIG. 15 are interconnected via a system bus 575. Additional subsystems such as a printer 574, a keyboard 578, a fixed disk 579, a monitor 576, which is coupled to a display adapter 582, and others are shown. Peripherals and input/output (I/O) devices, which couple to an I/O controller 571, can be connected to the computing system by any number of means known in the art, such as a serial port 577. For example, the serial port 577 or an external interface 581 can be used to connect the computing device to a wide area network such as the Internet, a mouse input device, or a scanner. The interconnection via the system bus 575 allows a programmed central processor 573 (e.g., a microprocessor, CPU, etc.) to communicate with each subsystem and to control the execution of instructions that may be stored in a system memory 572 or the fixed disk 579, as well as the exchange of information between subsystems. The system memory 572 and/or the fixed disk 579 may embody a computer-readable medium.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. An analytical system comprising:
   a storage container configured to store a plurality of capillaries;
   a transport bridge comprising a toothed belt, wherein the transport bridge is connected at a first end to the storage container, wherein the transport bridge is configured to transport a capillary in the plurality of capillaries via the toothed belt across the transport bridge;
   a gripper configured to receive the capillary after the capillary is transported across the transport bridge, wherein an end of the capillary is configured to contact a sample in a sample container and draw the sample in the capillary; and
   a reader configured to detect a signal from the sample in the capillary.

2. The analytical system of claim 1 wherein the transport bridge comprises an end comprising a loading ramp sloping down from the transport bridge.

3. The analytical system of claim 2 wherein the loading ramp comprises a toothed belt.

4. The analytical system of claim 2 further comprising a capillary rotator proximate an end of the loading ramp, wherein the capillary rotator is configured to rotate the capillary from a horizontal orientation to a vertical orientation.

5. The analytical system of claim 4 wherein the capillary rotator comprises a cavity configured to receive the capillary.

6. The analytical system of claim 4 further comprising a structure comprising a capillary lift surface between the rotator and the end of the loading ramp.

7. The analytical system of claim 1 wherein the storage container has an inclined surface on at least one side.

8. The analytical system of claim 7 further comprising a transport belt on the inclined surface.

9. The analytical system of claim 2 further comprising a sensor element proximate the loading ramp and configured to detect a presence of the capillary on the loading ramp.

10. The analytical system of claim 2 further comprising a crane assembly coupled to the transport bridge.

11. A method of using an analytical system comprising:
    transporting a capillary from a storage container storing a plurality of capillaries to a transport bridge comprising a toothed belt, wherein the transport bridge is connected at a first end to the storage container;
    transporting the capillary via a toothed belt across the transport bridge towards a reader;
    contacting the capillary with a sample to draw the sample into the capillary; and
    manipulating the capillary so that the sample in the capillary is read by the reader.

12. The method of claim 11 further comprising:
    transporting the capillary to a capillary lift surface; and
    receiving the capillary from the capillary lift surface in a cavity in a rotator.

13. The method of claim 11 wherein transporting the capillary on the transport bridge comprises transporting the capillary on a toothed belt of a loading ramp of the transport bridge.

14. The method of claim 11 further comprising:
    detecting a signal from the sample in the capillary by the reader.

15. The method of claim 14 further comprising, after detecting:
    determining a serum index value associated with a sample in the capillary.

16. The method of claim 11 further comprising:
manipulating the capillary using a crane assembly.

17. The method of claim 11 further comprising:
transporting the capillary from the transport bridge to a capillary lift surface;
receiving the capillary from the capillary lift surface in a cavity in a rotator, wherein the capillary rotator is configured to rotate from a horizontal orientation to a vertical orientation; and
rotating the rotator so that the rotator is in the vertical orientation.

18. The method of claim 11 wherein the storage container comprises an inclined surface.

19. The method of claim 11 wherein the reader comprises clamps for clamping the capillary.

20. The method of claim 11 further comprising:
inserting the capillary in a gripper after transporting the capillary and prior to contacting the capillary.

* * * * *